(12) United States Patent
Rothbauer et al.

(10) Patent No.: US 12,163,112 B2
(45) Date of Patent: Dec. 10, 2024

(54) PRODUCTION OF CELLULAR SPHEROIDS

(71) Applicant: Technische Universität Wien, Vienna (AT)

(72) Inventors: Mario Rothbauer, Pfaffstätten (AT); Peter Ertl, Vienna (AT); Christoph Eilenberger, Vienna (AT)

(73) Assignee: Technische Universität Wien, Vienna (AT)

( * ) Notice: Subject to any disclaimer, the term of this patent is extended or adjusted under 35 U.S.C. 154(b) by 1275 days.

(21) Appl. No.: 16/576,803

(22) Filed: Sep. 20, 2019

(65) Prior Publication Data

US 2020/0095526 A1    Mar. 26, 2020

(30) Foreign Application Priority Data

Sep. 21, 2018   (EP) ..................... 18195997

(51) Int. Cl.
| | |
|---|---|
| *C12M 3/06* | (2006.01) |
| *C12M 1/00* | (2006.01) |
| *C12M 3/00* | (2006.01) |
| *C12N 5/00* | (2006.01) |
| *C12N 5/09* | (2010.01) |

(52) U.S. Cl.
CPC ............ *C12M 23/16* (2013.01); *C12M 21/08* (2013.01); *C12M 23/20* (2013.01); *C12M 29/26* (2013.01); *C12M 47/02* (2013.01); *C12N 5/0062* (2013.01); *C12N 5/0693* (2013.01); *C12N 2513/00* (2013.01)

(58) Field of Classification Search
CPC ...... C12M 23/16; C12M 21/08; C12M 23/20; C12M 29/26; C12M 47/02; C12M 23/12; C12N 5/0062; C12N 5/0693; C12N 2513/00; C12N 2521/00; C12N 5/0068
See application file for complete search history.

(56) References Cited

U.S. PATENT DOCUMENTS

2009/0298116 A1* 12/2009 Fang ..................... B01L 3/5085
                                                                    430/320
2014/0057280 A1*  2/2014 Murthy ............ G01N 33/54386
                                                                    435/7.1

FOREIGN PATENT DOCUMENTS

CN         105733943 A   *   7/2016

OTHER PUBLICATIONS

Mehendale et al. "A Radial Pillar Device (RAPID) for continuous and high-throughput separation of multi-sized particles." Biomedical Microdevices vol. 20, Article No. 6 (2018) (Year: 2018).*
Cirello et al. "Multicellular spheroids from normal and neoplastic thyroid tissues as a suitable model to test the effects of multikinase inhibitors" Oncotarget .Feb. 7, 2017;8(6):9752-9766. (Year: 2017).*
Marel et al. "Arraying Cell Cultures Using PEG-DMA Micromolding in Standard Culture Dishes." Macromol Biosci. May 2013;13(5):595-602. (Year: 2013).*
Kim et al. "Fabrication of omega-shaped microwell arrays for a spheroid culture platform using pins of a commercial CPU to minimize cell loss and crosstalk." Biofabrication. Aug. 14, 2018;10(4):045003. (Year: 2018).*
Raghavan et al. "Comparative analysis of tumor spheroid generation techniques for differential in vitro drug toxicity." Oncotarget. Mar. 29, 2016; 7(13): 16948-16961. (Year: 2016).*

* cited by examiner

*Primary Examiner* — Titilayo Moloye
(74) *Attorney, Agent, or Firm* — Nevrivy Patent Law Group P.L.L.C.

(57) ABSTRACT

The present invention relates to a microfluidic device (1; 8) for the production of cellular spheroids comprising at least one chamber (2; 9) comprising a fluid inlet (3) for introducing fluid into the chamber (2; 9) and a fluid outlet (4) for removing said fluid from the chamber (2, 9), wherein said at least one chamber (2; 9) comprises a base formed by a substrate (5; 10) comprising at least two recesses (6; 11) to collect a fluid comprising biological cells when the substrate (5, 10) is contacted with the fluid, wherein the size of the at least two recesses (6; 11) decreases from the fluid inlet (3) to the fluid outlet (4) of the at least one chamber (2; 9).

18 Claims, 10 Drawing Sheets

PRODUCTION OF CELLULAR SPHEROIDS

The present invention relates to a microfluidic device, a system and a method for the production of cellular spheroids.

To understand the formation of tissue and organs, as well as diseases in vitro, conventional two-dimensional (2D) cell cultures are used to elucidate these questions. But 2D cell culture techniques do not faithfully replicate the mechanical and biochemical signals present in the body, since biology is clearly a complex 3D system. In 2D techniques, cell-to-surface interactions prevail rather than the crucial cell-to-cell and cell- to extracellular matrix (ECM) interactions that form the basis for normal cell function. However, over the last two decades, awareness of the relevance of the cellular microenvironment increased. This new cell culture paradigm, referred to as 3D cell culture, is rapidly gaining popularity. In contrast, three-dimensional (3D) cell cultures facilitate the production of homotypic or heterotypic cell cultures in a spatially relevant manner which mimic the natural microenvironment. Advantages of employing 3D cell cultures include the improved in vivo-like situation where cells are surrounded by its natural ECM and in direct cell contact with each other. In addition, the existence of extensive cell-cell and cell-ECM interactions, analogous to the in vivo situation, promote the recovery of natural structures and functions of the original tissue biology.

Multicellular spheroids are 3D cell aggregates that are a very promising model for assessing therapeutic treatments like chemotherapy, cell- and antibody based immunotherapy, gene therapy and combinatorial therapies. The 3D spheroid model can be used to improve the delivery system for compound penetration and targeting into tissues. 3D spheroids have shown an adaptive response to the recent advancements in microfluidic technologies which has allowed better control over spheroid sizes and subsequent drug screening studies. Microfluidic technology—also referred to as organ-on-a-chip is the adaptation, miniaturization, integration, and automation of analytical laboratory procedures into a single device or "chip".

Cellular spheroids are usually produced by using the hanging drop method. Thereby a fluid containing cells (e.g. eukaryotic cells, mammalian cells) is applied in individual droplets on an object slide in a hanging way (see e.g. Foty R (J Vis Exp. 2011; (51): 2720). The cells tend to join each other, whereby cellular spheroids are formed in the droplets after a certain amount of time. Each droplet contains one cellular spheroid. Such methods to produce cellular spheroids have several drawbacks. Surface tension limits the maximum size of a drop prepared by the hanging drop method, also, due to the small size of the suspended drops, evaporation is a large concern. As the water within the drop evaporates, the concentration of soluble components such as proteins and salts in the medium increases, subjecting the cells to a changing osmotic pressure, thus compromising their normal morphology and function. In order to avoid dehydration of the droplets and in order to supply additional cells and nutrients to the droplets to increase the size of the circular spheroids the droplets need to be carefully refilled from time to time. Most commonly, the droplets are refilled with a syringe having a fine needle. In order to avoid dripping of the droplets, refilling requires special care, since there is the risk that the droplets drop down from the object slide due to overfilling or due to trembling. In either way, an already formed cellular spheroid would be destroyed.

Hence, depending on the skills of a cultivator of the spheroids and his dexterity, many spheroids can be lost at once during cultivation. Due to that, the production can be very frustrating and time-consuming, especially if bigger cellular spheroids need to be produced.

Another disadvantage of the known production method is that only a few droplets can be applied to each object slide in order to avoid too much loss when the object slide is not handled carefully enough. Thus, a huge number of individual object slides are necessary to produce a sufficient quantity of cellular spheroids. Also the size of the single spheroids can be hardly influenced resulting in spheroids having different sizes.

Kwapiszewska et al. (Lab Chip, 2014, 14, 2096) describe a microfluidic chip for the cultivation of cellular spheroids of e.g. tumor cells.

In Zuchowska et al. (Electrophoresis, 2017, 38, 1206-1216), the effect of different concentrations of an anti-cancer agent on tumor cell spheroids, which were produced with a microfluidic system, is disclosed.

Patra et al. (Microfluidics, 2013, 7, 054114) describe a microfluidic device for the formation, cultivation and collection of spheroids, e.g. from carcinoma cells.

US 2016/097028 discloses a microfluidic device for the cultivation of spheroids and the harvesting of said spheroids from said device.

In WO 2017/188890 the enrichment and expansion of rare blood cells in a device comprising microwells is described.

WO 2018/067802 discloses microfluidic devices for high-throughput analysis of multiplex chemicals.

US 2009/298116 describes a cell culture device comprising microwells for the cultivation of three dimensional multicellular cell clusters.

Moshksayan et al. (Sensors and Actuators B, 2018, 263, 151-176) reviews several microfluidic designs for the formation and cultivation of spheroids.

It is an object of the present invention to provide means and methods to enhance and facilitate the production of cellular spheroids.

Hence, the present invention relates to a microfluidic device for the production of cellular spheroids comprising at least one chamber comprising a fluid inlet for introducing fluid into the chamber and a fluid outlet for removing said fluid from the chamber, wherein said at least one chamber comprises a base formed by a substrate comprising at least two recesses to collect a fluid comprising biological cells when the substrate is contacted with the fluid, wherein the size of the at least two recesses decreases from the fluid inlet to the fluid outlet of the at least one chamber.

Another aspect of the present invention relates to a microfluidic device for the production of cellular spheroids comprising at least one chamber comprising a fluid inlet for introducing fluid into the chamber and a fluid outlet for removing said fluid from the chamber, wherein said at least one chamber comprises a base formed by a substrate comprising at least one recess to collect a fluid comprising biological cells when the substrate is contacted with the fluid. Optionally such a device comprises at least two recesses, wherein the size of the at least two recesses may decrease from the fluid inlet to the fluid outlet of the at least one chamber.

The present invention relates also to a method for the production of cellular spheroids comprising the steps of:
applying a fluid comprising biological cells into at least one chamber of the device according to the invention and thus providing said fluid to the at least one recess; and incubating the device comprising said fluid for at least 2 hours until at least one cellular spheroid is formed in the at least one recess.

A further aspect of the present invention relates to a system for the production of cellular spheroids comprising at least one microfluidic device as defined herein.

Another aspect of the present invention relates to the use of a device or system as defined herein for the production of cellular spheroids.

It turned surprisingly out that a microfluidic device of the present invention shows exceptional capabilities to produce cellular spheroids in the at least two recesses of the base of the substrate. With the microfluidic device and method according to the invention it is possible to produce cellular spheroids in a reproducible, reliable and efficient manner in the at least one recess in the substrate.

One major advantage of the microfluidic device of the present invention is the possibility to produce cellular spheroids having a defined size/diameter is much more reproducible manner compared to other techniques like hanging drop cell cultures (see e.g. Foty R (J Vis Exp. 2011; (51): 2720). Another advantage using a microfluidic device of the present invention to produce cellular spheroids is the possibility to supply the cells with fresh culture medium during spheroid formation by simply providing a flow of culture medium during the production.

The provision of at least two recesses in the substrate of the device of the present invention allows the production of a random number of circular spheroids within one microfluidic device. Furthermore, by providing a plurality of recesses on the substrate cellular spheroids can be produced very cost-efficient. Preferably, the microfluidic device according to the invention has between 15 and 30 recesses.

The at least two recesses have a different size and shape. This has the advantage, that different sized cellular spheroids can be produced within one single microfluidic device.

The size of the at least two recesses decreases from the fluid inlet to the fluid outlet of the at least one chamber. Therefore, the smallest recess/recesses is/are located closest to the fluid outlet. As explained herein, by rinsing the at least one chamber with the discharging fluid at different velocities the cellular spheroids can be eluted according to their size. Since the smallest recess/recesses is/are arranged closest to the outlet and the rest of the recesses are arranged in an ascending manner towards the inlet, the advantage is obtained that by eluting the cellular spheroids according to their size starting out with the smallest recess/recesses eluted cellular spheroids cannot get stuck in other recesses still containing cellular spheroids.

A "cellular spheroid", as used herein, is a three-dimensional cell aggregate in the form of a spheroid or having a spheroid-like form. Such spheroids can also be considered as "organoids". "Cellular spheroids" can be formed by eukaryotic, in particular mammalian cells (e.g. human cells), whereby particularly preferred cells are cells being present in organs and tissues of mammals. These spheroids may comprise one or more type of cells. The use of different type of cells allows to produce more complex "organoids" or tissue-like structures.

The microfluidic device according to the invention comprises at least one chamber comprising a fluid inlet for introducing fluid into the chamber and a fluid outlet for removing said fluid from the chamber. Said at least one chamber comprises a base formed by a substrate comprising at least two recesses to collect a fluid comprising biological cells when the substrate is contacted with said fluid.

Preferably, the fluid comprising the biological cells also contains nutrients to supply the cells.

In a preferred embodiment of the microfluidic device according to the invention, the fluid inlet and the fluid outlet are positioned to direct fluid flowing from the fluid inlet to the fluid outlet through the chamber. With the fluid inlet and the fluid outlet, the fluid containing the biological cells can be supplied to the at least two recesses in an easy and controllable manner, whereby the risk of destroying a circular spheroid growing in the at least one recess is reduced to a minimum. Preferably, the fluid inlet and the fluid outlet are provided with a coupling in order to enhance the connectability of the fluid inlet and fluid outlet. The coupling can be, for example, a Luer Lock connection or a simple Luer-connection.

In a further preferred embodiment of the present invention the substrate of the microfluidic device comprises, consists of or is coated at least partially with a biocompatible material. Preferably, the biocompatible material is a silicone or a plastic material or glass. In particular, the biocompatible material is preferably selected from the group consisting of a polystyrene, cycloolefin-copolymer, polymethylmethacrylate, cyclo-olefin polymer, polydimethylsiloxane, polycarbonate (PC), polypropylene (PP), polyvinylchloride (PVC), perflouropolyether (PFPE), polyurethane, poly(ethyleneterephthalate) (PET), polyester and thiol-enes. Using a biocompatible material for the substrate or coating the substrate with a biocompatible material has the advantage, that the cells of the cellular spheroid are not affected and hence probably intoxicated by the substrate. In another preferred embodiment of the microfluidic device according to the invention, the whole at least one chamber consists of or is coated with a biocompatible material.

In another preferred embodiment of the microfluidic device according to the invention the at least two recesses and/or the substrate is/are coated at least partially with an anti-fouling layer. The use of an anti-fouling layer reduces or prevents the deposition of substances present in culture media or washing solutions as well as of cells within the microfluidic device.

Preferably, the anti-fouling layer is selected from a material of the group consisting of:
  polyethylene glycol (PEG)-based polymers, preferably PLL-g-PEG or PEGS having different lengths, varying from about 22 to 450 repeating units, and/or corresponding to a molecular weight in the range of 1000 to 20000 Da;
  polybetaines, such as poly(sulfobetaine) (PSB) or poly(carboxybetaine) (PCB);
  polyampholytes;
  fluorinated-polymers;
  polysaccharides, such as agar or agarose;
  polyhdroxy-polymers, such as poly(2-hydroxyethyl methacrylate (poly-HEMA) or poly-hydroxypropyl methacrylate (poly-HPMA),
  poly(ethylene oxide);
  hydroxypropyl methylcellulose (HPMC);
  poly(vinyl alcohol) (PVA);
  poly(2-hydroxyethyl methacrylate) (pHEMA);
  poly(acrylic acid) (PAA);
  dextran;
  hydroxylethylcellulose (HEC);
  natural biopolymers (hydrophobines, S-layer protein SbpA);
  anti-fouling nanointerfaces such as polyelectrolyte multilayers (PEMs) or self-assembled monolayers (SAMs);

nonionic surfactants such as polyoxyethylene dodecanol, Tween-20, n-dodecyl-D-maltoside (DDM) and pluronics (triblock copolymers PEO-b-poly(propylene oxide)-b-PEO); and silanes such as 3-glycidoxypropyltrimethoxysilane (GPTMS) and 3-chloropropyltrichlorosilane (CPTMS) and (3-aminopropyl)triethoxy silane (APTES).

The anti-fouling layer prevents the adhesion of debris as well as the adhesion of the at least one cellular spheroid on a surface of the at least two recesses. Thereby, the at least two recesses cannot only be easily cleaned, it is also easier to remove the cellular spheroid from the at least two recesses once it has reached its predetermined size. In another preferred embodiment of the microfluidic device according to the invention, the at least one chamber is also at least partially coated with an anti-fouling layer.

Preferably, the at least two recesses have the shape of a hemisphere, a spherical cap, a semi ellipsoid, a cone, a truncated cone, a terraced cone, a pyramid, a truncated pyramid, a terraced pyramid, a torus, or an elliptic paraboloid. Especially with two recesses in the shape of a hemisphere, remarkably round cellular spheroids can be produced with the microfluidic according to the invention. Please see the examples listed below.

With the at least two recesses having the shape of a spherical cap the spherical cap has a polar angle $\alpha$ of 30° to 90°, preferably 40° to 90°, more preferably 50° to 90°, more preferably 60° to 90°, more preferably 70° to 90°, more preferably 80° to 90°, more preferably 85° to 90°.

With the at least two recesses having the shape of an elliptic paraboloid at least a part of a shell surface of the paraboloid is formed by a parable with the formula $y=A*x^B$ rotated in space, wherein A is between 0.05 and 10, preferably 0.05, 0.1, 0.25, 0.5, 0.75, 1, 2, 3, 4, 5, 6, 7, 8, 9 or 10 and B is 2, 4 or 6.

With the at least two recesses having the shape of a spherical cap or a elliptic paraboloid according to the configuration explained above a single round cellular spheroid with a roundness factor $\geq 0.9$ forms in the at least two recesses. The roundness factor calculates according to the following formula:

roundness factor=$(4*area)/(\pi*\text{max diameter}^2)$;

with the area corresponding to an area measured in a 2D image of the cellular spheroid in top view, which corresponds also to the projected area of the cellular spheroid in top view, with $\pi$ corresponding to PI and with the max. diameter corresponding to the max. diameter of the area measured in the 2D image of the cellular spheroid in top view. The roundness factor is an indicator of the circularity of the projected area of the spheroids.

Advantageously, the at least two recesses have a depth of 50 μm to 1 mm, preferably 50 μm to 800 μm, more preferably 50 μm to 500 μm.

Advantageously, the at least two recesses have a width or diameter of 100 μm to 2 mm, preferably 100 μm to 1.5 mm, more preferably 100 μm to 1 mm.

Advantageously, the ratio of depth to width of the at least two recesses is between 1 to 1 and 1 to 3, preferably 1 to 1 to 1 to 2.

Practically, the at least two recesses are spaced apart from each other at a distance from 10 μm to 6 mm, preferably 20 μm to 6 mm, more preferably 30 μm to 6 mm, more preferably 50 μm to 6 mm, more preferably 70 μm to 6 mm, more preferably 100 μm to 6 mm, more preferably 100 μm to 5 mm more preferably 100 μm to 4 mm.

In another preferred embodiment of the microfluidic device according to the invention, the at least two recesses are grouped and the recesses of each group have the same size and/or the same shape and the recesses of different groups have different sizes or different sizes and different shapes. Preferably, each group includes at least three recesses, which are advantageously arranged in a row.

Preferably, one group of recesses is spaced apart to another group of recesses at a distance of 200 μm to 10 mm.

Preferably, the at least one cellular spheroid formed in at least two recesses is eluted by rinsing the at least one chamber with a discharging fluid at a velocity sufficient to elute the cellular spheroid.

Preferably, with a substrate comprising at least two recesses of different size the cellular spheroids are eluted by successively rinsing the at least one chamber with a discharging fluid at different velocities. This has the advantage that the cellular spheroids are already sorted according to their size after elution. A subsequent separation is therefore not necessary. The velocity of a discharging fluid at which spheroids of a specific size are removed from the at least one recess of the substrate can be tested empirically within the ranges mentioned below because it may depend on the density as well as the cell type of the cells.

Preferably, the velocities for eluting the circular spheroids are chosen to elute the cellular spheroids according to their size, width or diameter. Preferably, the velocity for eluting the at least one cellular spheroid is in the range of 0.5 μL/min to 120 μL/min. More preferably, the velocity for eluting the at least one cellular spheroid is at least 100 μL/min for a recess with a width or diameter between 900 μm and 1000 μm, is at least 30 μL/min for a recess with a width or diameter between 500 μm and 700 μm and/or is at least 20 μL/min for a recess with a width or diameter between 150 μm and 300 μm.

In another preferred embodiment of the microfluidic device according to the invention, the at least on chamber rejuvenates from the fluid inlet to the fluid outlet. This has the advantage, that a velocity of the fluid flowing through the at least one chamber can be changed in the chamber.

Another aspect the present invention relates to the production of cellular spheroids comprising the steps of applying a fluid comprising biological cells into at least one chamber of a device according to the invention and thus providing said fluid to the at least two recesses and incubating the device comprising said fluid for at least 2 hours until at least one cellular spheroid is formed in the at least two recesses.

Preferably, in the inventive method the microfluidic device comprising said fluid comprising biological cells is incubated for a maximum of six months, preferably for a maximum of three months, more preferably for a maximum of one month, preferably for a maximum of 14 days, preferably for a maximum of 7 days, preferably for a maximum of 96 h, preferably for a maximum of 72 h, preferably for a maximum of 48 h. More preferably, the device comprising said fluid comprising biological cells is incubated for one to seven days. The growth of the cellular spheroids depends essentially on the incubation time, the amount of cells supplied and/or the size of the recesses.

In a preferred embodiment of the method according to the invention, the fluid comprising biological cells is applied into the at least on chamber with a velocity in the range of 4 μL/min to 8 μL/min.

Another aspect of the present invention relates to a system for the production of cellular spheroids comprising at least one microfluidic device according to the present invention.

The system according to the invention comprises at least one microfluidic device according to the invention, preferably a plurality of microfluidic devices according to the invention. This has the advantage, that a plurality of cellular spheroids can be produced in a reliable and cost efficient manner Part of the system of the present invention are pumps and pipes to move fluids within the device of the present invention.

Preferably, the system according to the invention comprises a gradient generator, wherein each of the at least one microfluidic device is fluidly connected via the fluid inlet to a fluid outlet of the gradient generator. In order to provide different substances to the gradient generator independently simultaneously, the gradient generator practically comprises at least two fluid inlets.

A system according to the present invention comprising a gradient generator can be used in the assessment of the influence of substances on the cells within cellular spheroids as obtained by the method of the present invention. In particular, the system and the devices of the present invention can be used for the screening of chemical libraries of synthetic molecules, natural products or extracts, traditional small-molecule drugs, usually derived from chemical synthesis, and biopharmaceuticals, which include recombinant proteins, vaccines, blood products used therapeutically (such as intravenous immunoglobulins), gene therapy, monoclonal antibodies and cell therapy (for instance, stem-cell therapies). The application of varying concentrations of a compound on cellular spheroids allows the determination whether a substance has beneficial or negative effect on cells within a cellular spheroid. Such a method can be used, for instance, to identify doses of compounds which may have beneficial, toxic, inhibitory and/or stimulating effects on cellular spheroids. Thus, the system according to the present invention can be used for determining the influence of varying substance concentrations on cellular spheroids.

A further aspect of the present invention relates to the use of the device according to the present invention or the system according to the invention for the production of cellular spheroids.

For some uses, for example the identification of immunofluorescence and biochemical staining-protocols for micro tissues and organ spheroids, it is advantageous that the spheroids, in particular the cells forming the spheroids, are labelled with antibodies or functional fragments thereof specifically binding to said cells. Hence, in a particularly preferred embodiment of the present invention the spheroids within the at least two recesses are incubated with at least one antibody binding specifically to the biological cells forming the spheroids. The at least one antibody may be a monoclonal, a recombinant and polyclonal antibody, their subclasses immunoglobulin A, D, E, G, M, W, Y, an aptamer, and/or human or animal antibodies (e.g. rat, mouse, goat, rabbit, horse, donkey, etc.). In order to label the spheroids with antibodies an antibody comprising fluid, preferably a buffer exhibiting preferably a physiological pH, is applied to the device of the present invention.

According to a preferred embodiment of the present invention the at least one antibody is labelled with:
a fluorophore;
a peroxidase (POD, horseradish peroxidase HRP); whereby one of the following peroxidase substrates can be used preferably to detect binding of said antibodies to the spheroids and their respective cells:
ABTS (2,2'-azino-bis(3-ethylbenzothiazoline-6-sulphonic acid)),
AEC (3-Amino-9-ethylcarbazol),
CN (4-Chlor-1-naphthol),
DAB (3,3'-Diaminobenzidin),
Luminol and andere Dioxetane,
TMB (Tetramethylbenzidin),
an alkaline phosphatase (AP); whereby one of the following phosphatase substrates can be preferably used to detect binding of said antibodies to the spheroids and their respective cells:
5-brom-4-chlor-3-indoxylphosphat (BCIP),
naphthol-AS-MX-Phosphat,
neufuchsin,
radioisotope; whereby the radioisotope is preferably selected from one of the following isotopes:
$^{131}$iod
$^{32}$phosphor
$^{3}$tritium These and further advantageous embodiments of the invention will be explained based on the following description and the accompanying drawings. The person skilled in the art will understand that various embodiments may be combined.

Figure 1:
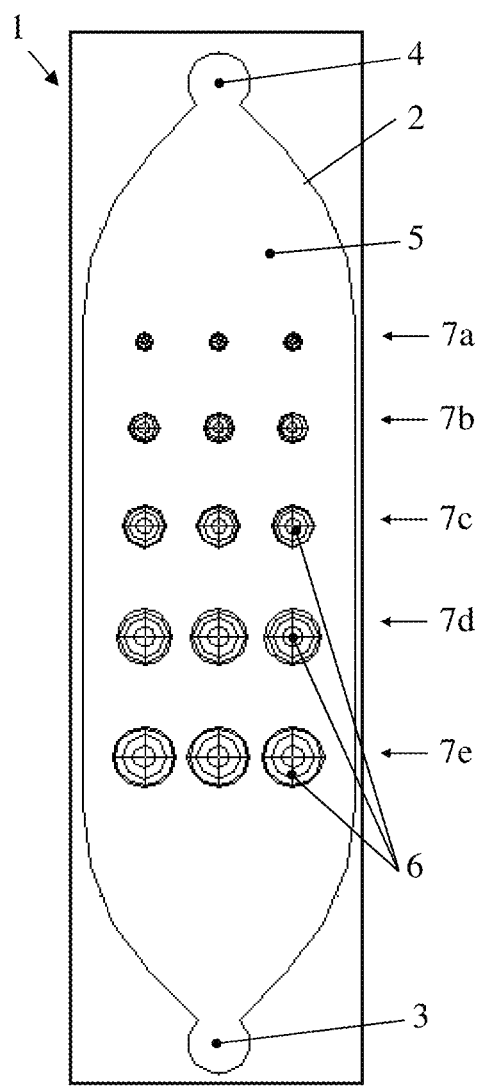
FIGS. 1 and 2 show in a schematic plan view an embodiment of a microfluidic device according to the invention.
Figure 2:
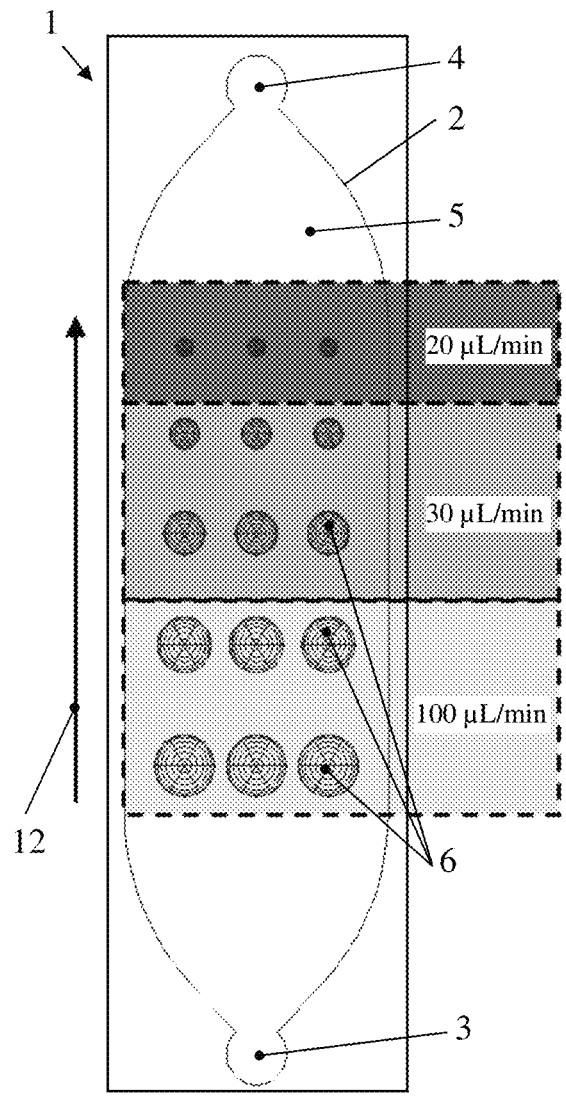

FIGS. 1 and 2 show in a schematic plan view an embodiment of a microfluidic device 1 according to the invention. The microfluidic device 1 comprises a chamber 2 having a fluid inlet 3 for introducing fluid into the chamber 2 and a fluid outlet 4 for removing said fluid from the chamber 2. Moreover, the chamber 2 comprises a base formed by a substrate 5, which substrate 5 comprises fifteen recesses 6.

The recesses 6 are grouped in groups 7a to 7e, wherein each group 7a to 7e includes three recesses 6 arranged in a row. The recesses 6 of each group 7a to 7e have the same size and the same shape and the recesses of different groups 7a to 7e have different sizes. For example, the recesses 6 of the first group 7a have a diameter of 200 µm, the recesses 6 of the second group 7b have a diameter of 500 µm, the recesses 6 of the third group 7c have a diameter of 700 µm, the recesses 6 of the fourth group 7d have a diameter of 900 µm and the recesses 6 of the fifth group 7e have a diameter of 1000 µm.

In order to grow cellular spheroids fluid comprising biological cells is applied into the chamber 2 through the fluid inlet 3. Consequently, the substrate 5 is contacted with the fluid and the recesses 6 are filled with the fluid. Depending on the required size of the cellular spheroids an incubation time needs to be met before the cellular spheroids can be eluted from the chamber 2. Smaller cell formation form already after two hours.

In order to elute the cellular spheroids from the recesses a discharging fluid is applied through the fluid inlet 3 to rinse the chamber 2. The discharging fluid is discharged through the fluid outlet 4. The discharging fluid flows through the chamber 2 in the direction 12. Please see FIG. 2. Preferably the discharging fluid is supplied through the fluid inlet 3 at different velocities in order to elute the cellular spheroids according to their size or, respectively in groups according to their size.

In the example shown in FIG. 2 the discharging fluid is supplied to the fluid inlet 3 with a first low velocity sufficient to elute the smallest circular spheroids from the recesses 6 of the group 7a first. The first velocity is 20 µL/min, for example. In a further step the velocity of the discharging fluid is increased to a second velocity. The second velocity is 30 µL/min, for example. Due to that, the cellular spheroids formed in recesses 6 of the groups 7b and 7c are eluted. By further increasing the velocity to a third velocity, for example to 100 µL/min, the rest of the circular spheroids of the recesses 6 of the groups 7d and 7e are be eluted. Please note, that with a finer graduation of the velocity the cellular spheroids formed in the groups 7b and 7d can also be eluted individually per group. Please not, that the velocities shown in FIG. 2 are only illustrative and can differ from this values depending on the size of the recesses 6. Furthermore, please note that for the elution of the cellular spheroids it is also possible that the discharging fluid is applied through the fluid inlet 3 with a velocity sufficient to elute all cellular spheroids at once from the chamber 2.

After all cellular spheroids are eluted, the microfluidic device 1 is cleaned with a cleaning fluid and ready for further use.

Preferably, the fluid comprising the biological cells is applied to the chamber 2 in a continuous manner through the fluid inlet 3 and discharged out of the chamber 2 by the outlet 4 during incubation. This has the advantage that the cells can be continuously supplied with nutrients and that new cells are supplied to the microfluidic device 1.

Figure 3:
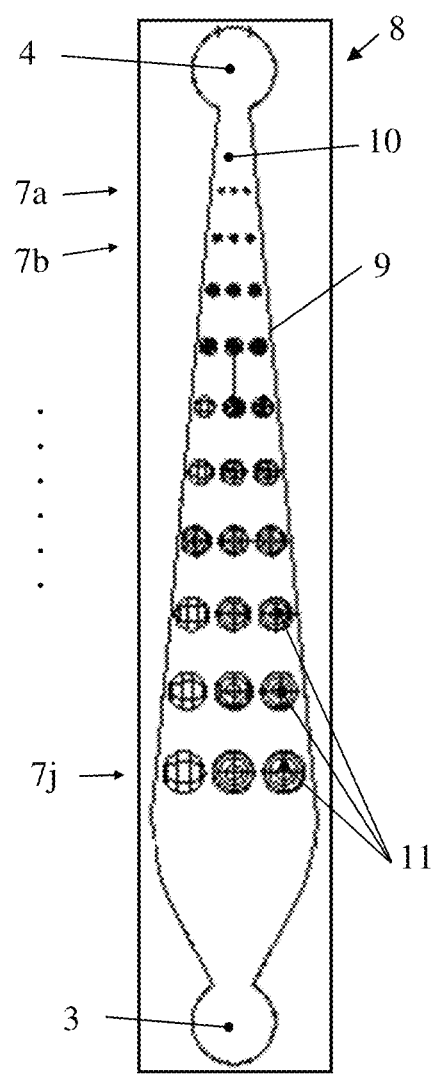
FIG. 3 shows in a schematic plan view another embodiment of a microfluidic device according to the invention.

FIG. 3 shows in a schematic plan view of another embodiment of a microfluidic device 8 according to the invention. The microfluidic device 8 distinguishes to the microfluidic device 1 according to FIG. 1 in the fact that a chamber 9 of the microfluidic device 2 essentially rejuvenates from the fluid inlet 3 to the fluid outlet 4 and in the fact that the substrate 10 comprises five more groups 7f to 7j of different sized recesses 11, which leads to thirty recesses 11. Due to the rejuvenation the velocity of fluid rinsing through a chamber 9 is changed. Higher velocities result in higher shear forces on the cellular spheroids. Thus, an impact on the cellular spheroids at different shear forces can be monitored in one single channel. For example, with a fluid applied with a volume velocity of 8 µL/min at the inlet 3 at the microfluidic device 8 shown in FIG. 3 a shear force at a wider part of the chamber 9 is 0.01 dyn/cm$^2$ and a shear force near the fluid outlet is 0.07 dyn/cm$^2$. Accordingly, the shear forces near the fluid outlet are seven times as high as the shear forces at the wider part of the chamber 9.

Elements of the micro fluidic device 8 being similar to elements of the microfluidic device 1 according to FIG. 1 are indicated with the same reference numerals. Please note that substrate 10 can also comprise a different amount of recesses 11.

Figure 4:
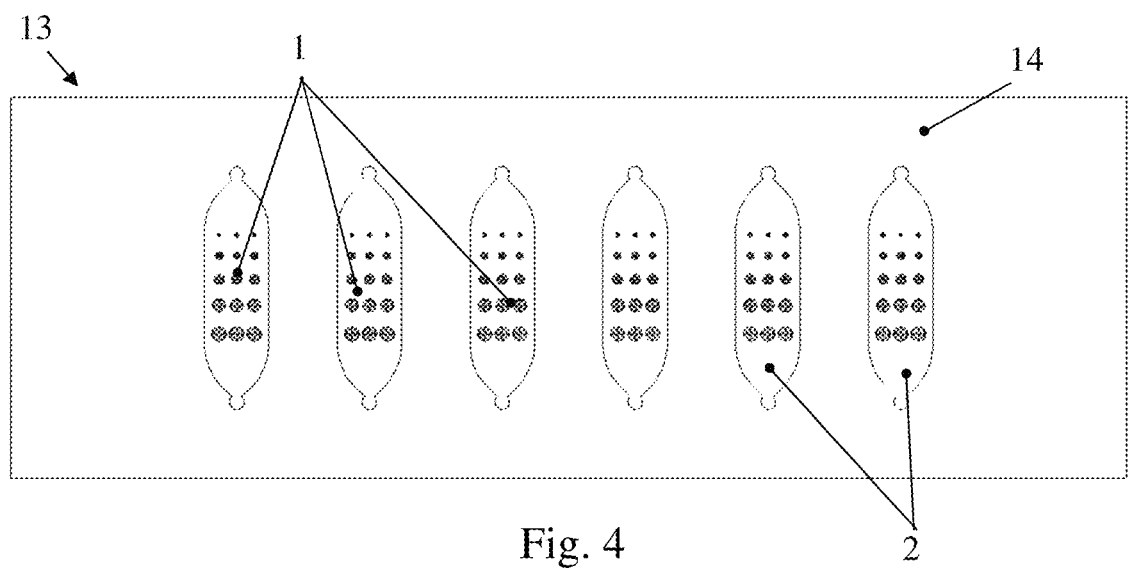
FIG. 4 shows in a schematic plan view an embodiment of a system according to the invention.

FIG. 4 shows in a schematic plan view an embodiment of a system 13 according to the invention. The system 13 comprises six microfluidic devices 1 according to FIG. 1. The system 13 has one base 14, in which the individual chambers 2 of the microfluidic devices 1 are contained.

Figure 5A:
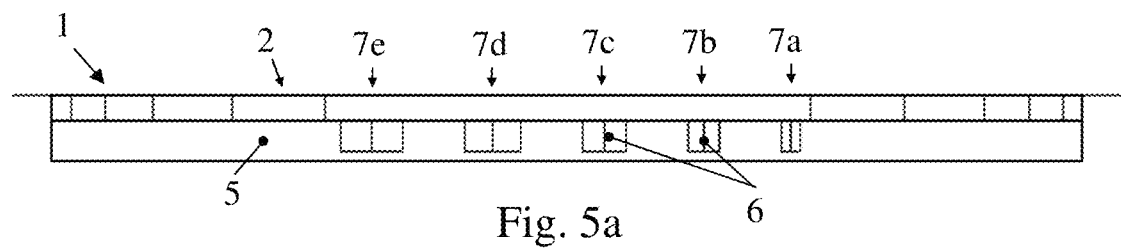
FIG. 5a shows a sectional side view of the embodiment of the microfluidic device according FIG. 1 with cylindrical shaped recesses.

FIG. 5a shows a sectional side view of the embodiment of the microfluidic device 1 according to FIG. 1 with cylindrical shaped recesses 6.

Figure 5B:
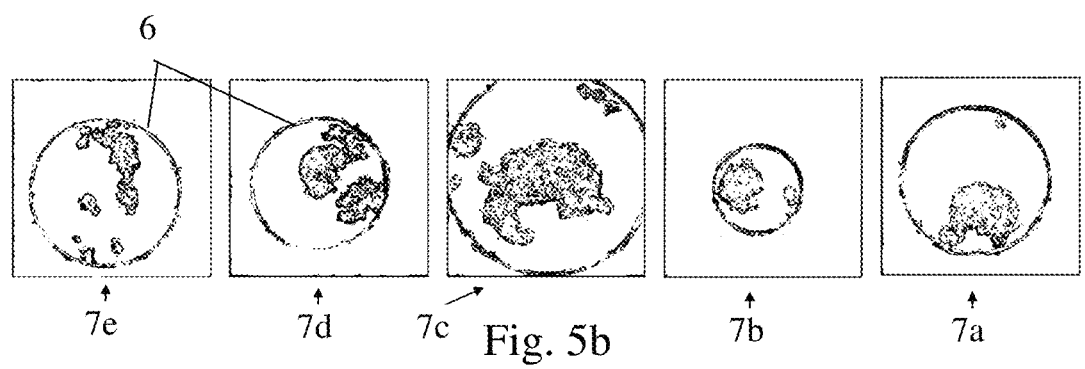
FIG. 5b shows schematically pictures of cell formations formed in the embodiment of the microfluidic device according to FIG. 5a in a plan view.

FIG. 5b shows schematically pictures of cell formations formed in the embodiment of the microfluidic device 1 according to FIG. 5a in a plan view. Due to simplicity reasons FIG. 5b only shows one example of a cell formation per recesses 6 of each group 7a to 7e. To indicate which picture corresponds to which group 7a to 7e, the pictures are indicated with the group reference numerals.

As can be seen in the pictures of FIG. 5b, there is no spherical cell formation in cylindrical shaped recesses 6. Rather a multitude of cell formations of different form develop in cylindrical shaped recesses 6.

Figure 6A:
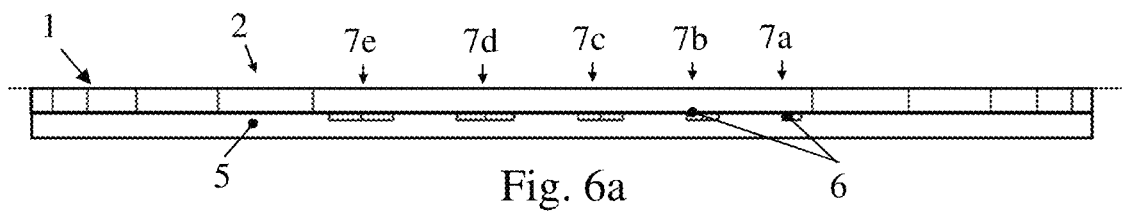
FIG. 6a shows a sectional side view of the embodiment of the microfluidic device according to FIG. 1 with disc-shaped recesses.

FIG. 6a shows a sectional side view of the embodiment of the microfluidic device 1 according to FIG. 1 with disc-shaped recesses 6.

Figure 6B:
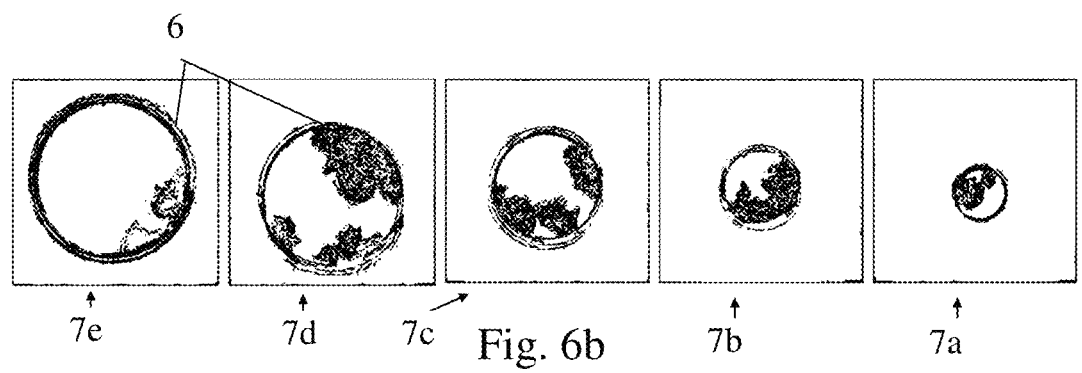
FIG. 6b shows schematically pictures of cell formations formed in the embodiment of the microfluidic device according to FIG. 6a in a plan view.

FIG. 6b shows schematically pictures of cell formations formed in the embodiment of the microfluidic device according to FIG. 6a in a plan view. Due to simplicity reasons FIG. 6b only shows one example of a cell formation per recesses 6 of each group 7a to 7e. To indicate which picture corresponds to which group 7a to 7e, the pictures are indicated with the group reference numerals.

As can be seen in the pictures of FIG. 6b, there is no spherical cell formation in disc-shaped recesses 6. Also with disc-shaped recesses 6 a multitude of cell formations of different form develop in the recesses 6.

Figure 7A:
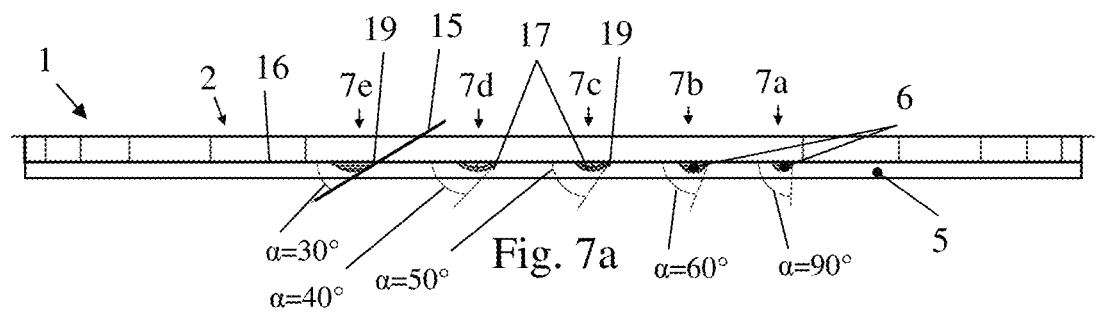
FIG. 7a shows a sectional side view of the embodiment of the microfluidic device according to FIG. 1 with recesses having the shape of spherical caps.

FIG. 7a shows a sectional side view of the embodiment of the microfluidic device 1 according to FIG. 1 with recesses 6 having the shape of spherical caps. The spherical caps have different angles α. The angle α is the angle between a tangent plane 15 in an exemplary point 19 on a surface 17 of the spherical cap and a horizontal plane 16 of the substrate 5, wherein in the point 19 the surface 17 of the spherical cap intersects with the horizontal plane 16 of the substrate. Since the angle α corresponds to the polar angle of the spherical cap, α is hereinafter referred to as the polar angle.

The spherical caps of different groups 7a to 7e have the same depth but vary in their diameter and hence, also in their polar angle α. For example, group 7a, which contains the smallest recesses 6, has a polar angle α of 90° and group 7e has a polar angle α of 30°. Please note that spherical caps of different groups 7a to 7e can also have the same diameter with different polar angles α or can also have different depths and diameters with the same gradient angels α.

Figure 7B:
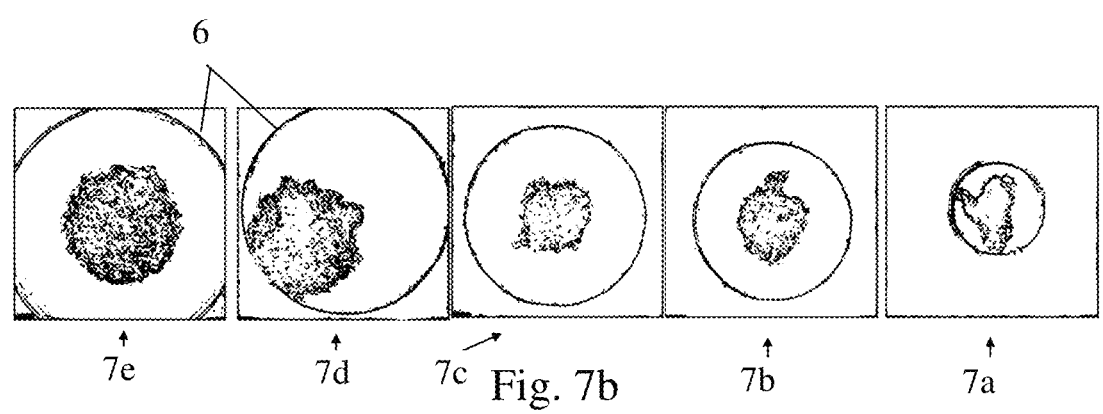
FIG. 7b shows schematically pictures of cell formations formed in the embodiment of the microfluidic device according to FIG. 7a in a plan view.

FIG. 7b shows schematically pictures of cell formations formed in the embodiment of the microfluidic device 1 according to FIG. 7a in a plan view. Due to simplicity reasons FIG. 7b only shows one example of a cell formation per recesses 6 of each group 7a to 7e. To indicate which picture corresponds to which group 7a to 7e, the pictures are indicated with the group reference numerals.

As can be seen in the pictures of FIG. 7b cellular spheroids form in the spherical cap shaped recesses 6.

Figure 8A:
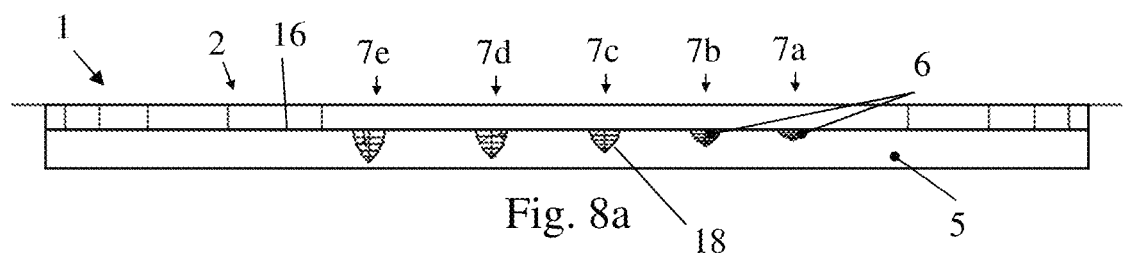
FIG. 8a shows a sectional side view of the embodiment of the microfluidic device according to FIG. 1 with recesses having the shape of elliptical paraboloids.

FIG. 8a shows a sectional side view of the embodiment of the microfluidic device 1 according to FIG. 1 with recesses 6 having the shape of elliptical paraboloids. A shell surface 18 of the elliptic paraboloids is formed by a parable with the formula $y=A*x^B$ rotated in space. The recesses 6 of different groups 7a to 7e have the same diameter but vary in their depth and hence in their elliptical paraboloid shape. For example, the recesses 6 of group 7a, which are the smallest recesses 6, are formed by a parable with the formula $y=0.1*x^2$ rotated in space and the recesses 6 of group 7e are formed by a parable with the formula $y=2*x^2$ rotated in space. Please note that the recesses 6 of different groups 7a to 7e can also have the same depth with a different elliptical paraboloid shapes or can also have different depths and/or diameters with the same elliptical paraboloid shape.

Figure 8B:
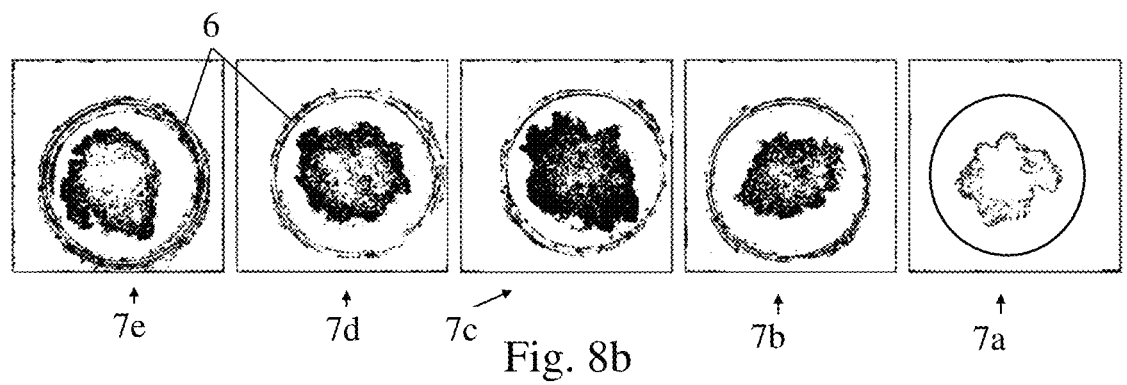
FIG. 8b shows schematically pictures of cell formations formed in the embodiment of the microfluidic device according to FIG. 8a in a plan view.

FIG. 8b schematically shows pictures of cell formations formed in the embodiment of the microfluidic device according to FIG. 8a in a plan view. Due to simplicity reasons FIG. 8b only shows one example of a cell formation per recesses 6 of each group 7a to 7e. To indicate which picture corresponds to which group 7a to 7e, the pictures are indicated with the group reference numerals.

As can be seen in the pictures of FIG. 8b cellular spheroids form in the elliptical paraboloid shaped recesses 6.

Figure 9A:
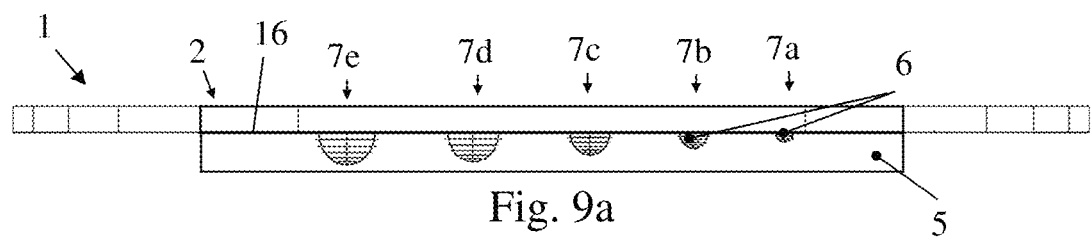
FIG. 9a shows a sectional side view of the embodiment of the microfluidic device according to FIG. 1 with hemispherical shaped recesses.

FIG. 9a shows a sectional side view of the embodiment of the microfluidic device 1 according to FIG. 1 with hemispherical shaped recesses 6.

Figure 9B:
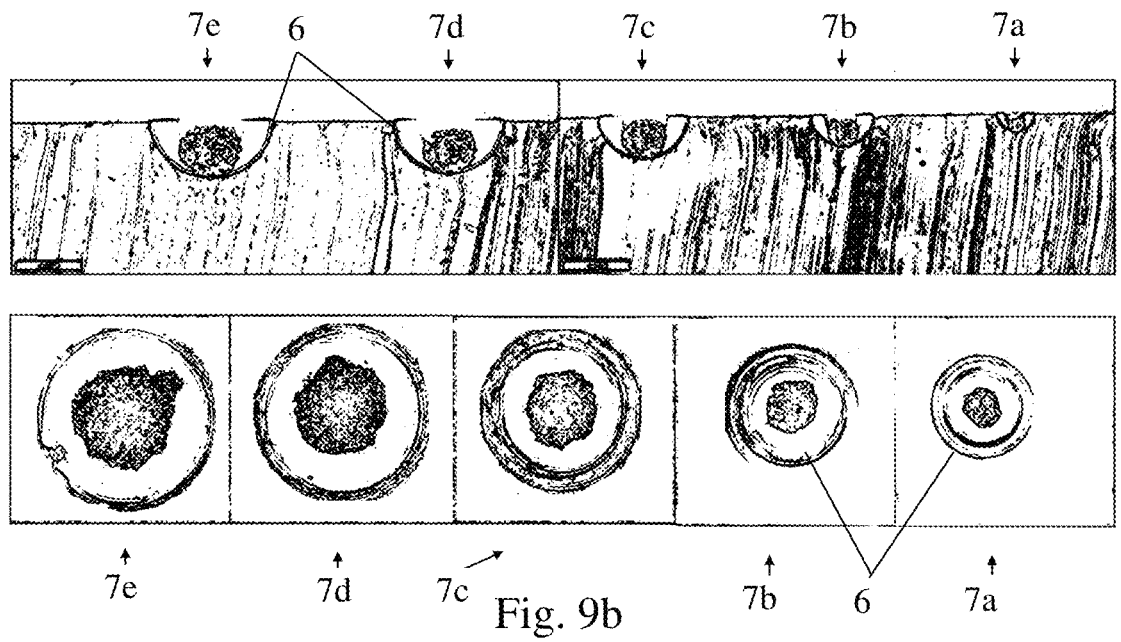
FIG. 9b shows schematically pictures of cell formations formed in the embodiment of the microfluidic device according to FIG. 9a in a plan view and in a sectional side view.

FIG. 9b schematically shows pictures of cell formations formed in the embodiment of the microfluidic device 1 according to FIG. 9a in a plan view and in a sectional side view. Due to simplicity reasons FIG. 9b only shows one example of a cell formation per recesses 6 of each group 7a to 7e in the plan view and in the sectional side view. To indicate which recess 6 belongs to which group 7a to 7e, the recesses 6 are indicated with the group reference numerals.

As can be seen in FIG. 9b, perfectly round cellular spheroids form in hemispheric shaped recesses 6.

Figure 10:
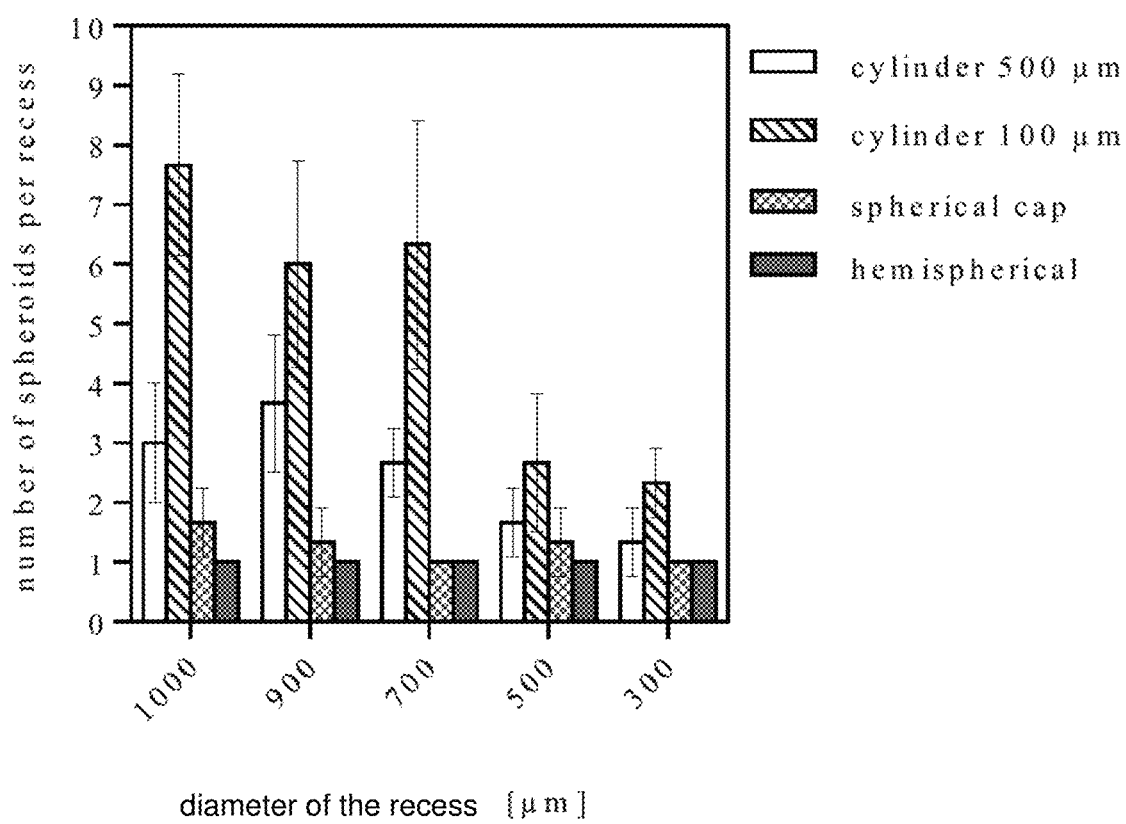
FIG. 10 shows a graph with the number of spheroids per recess over the diameter of the recess.

FIG. 10 shows a graph with the number of spheroids per recess over the diameter of the recess.

Figure 11:
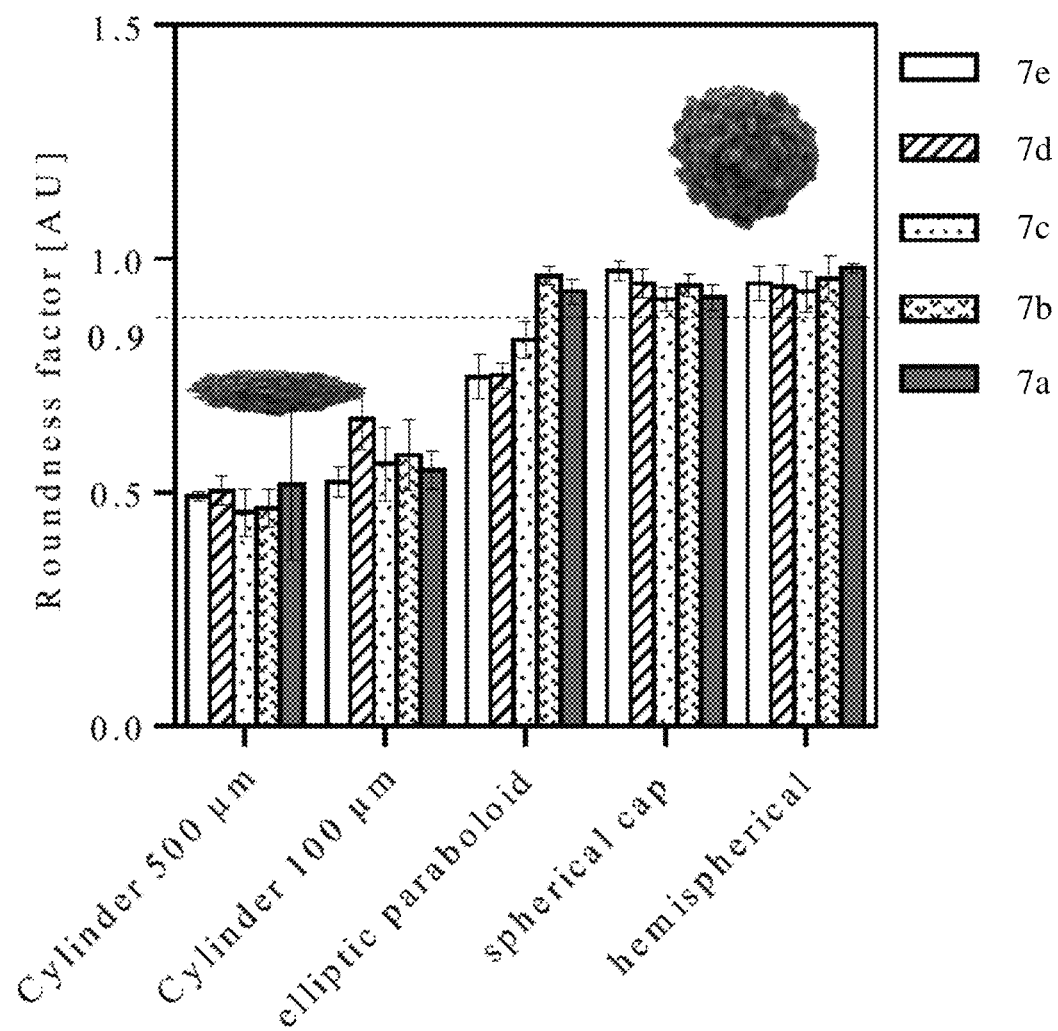
FIG. 11 shows a graph showing the roundness factor of the cellular spheroids over different shaped and sized recesses.
Figure 12:
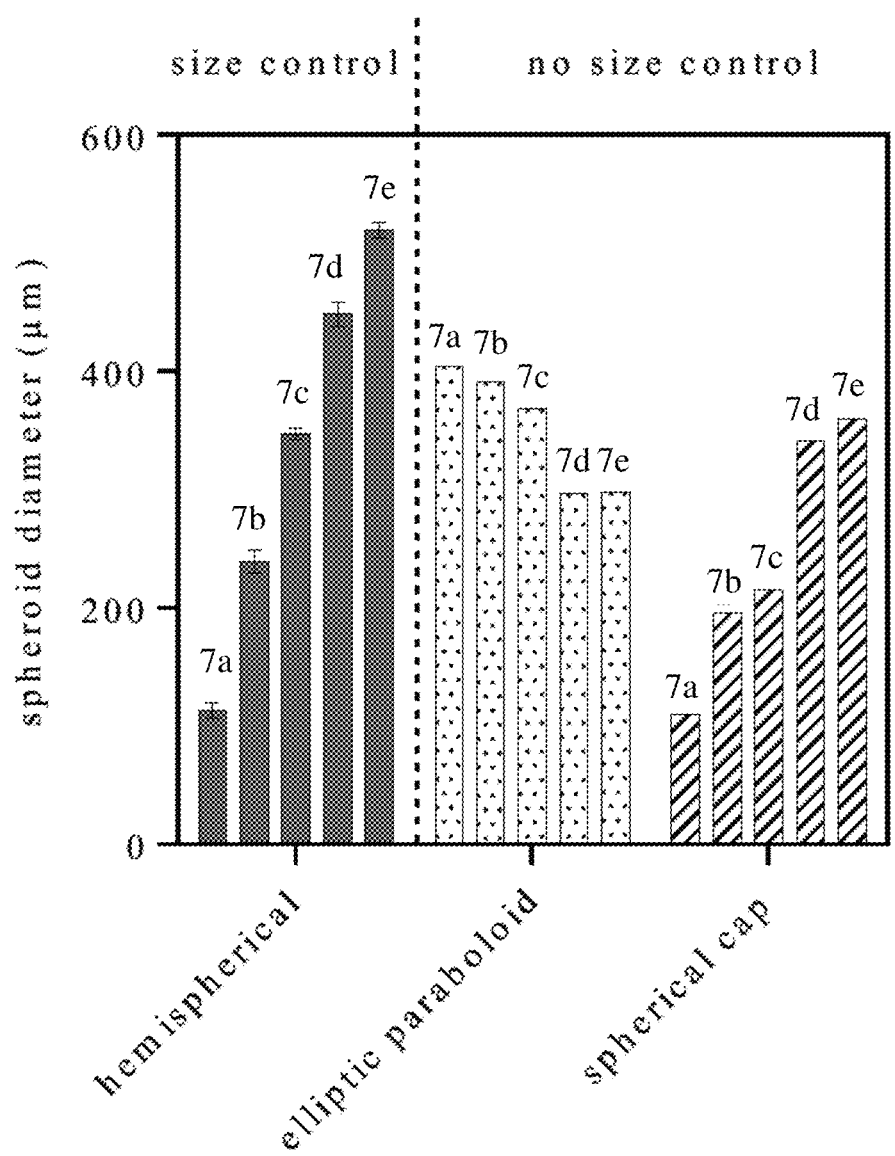
FIG. 12 shows a graph with the spheroid diameter over different shaped recesses.
Figure 12:
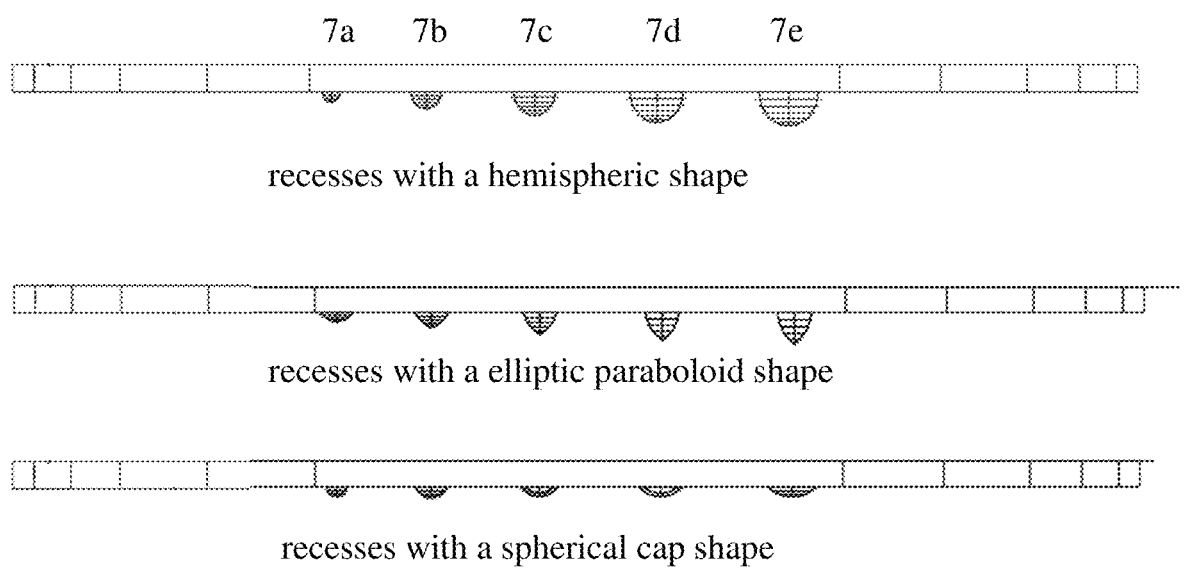

FIG. 11 shows a graph showing the roundness factor of the cellular spheroids over different shaped and sized recesses 6, wherein the size 7a to 7e of the recesses 6 is organized according to FIG. 12.

FIG. 12 shows a graph with the spheroid diameter over different shaped recesses having different size.

Figure 13:
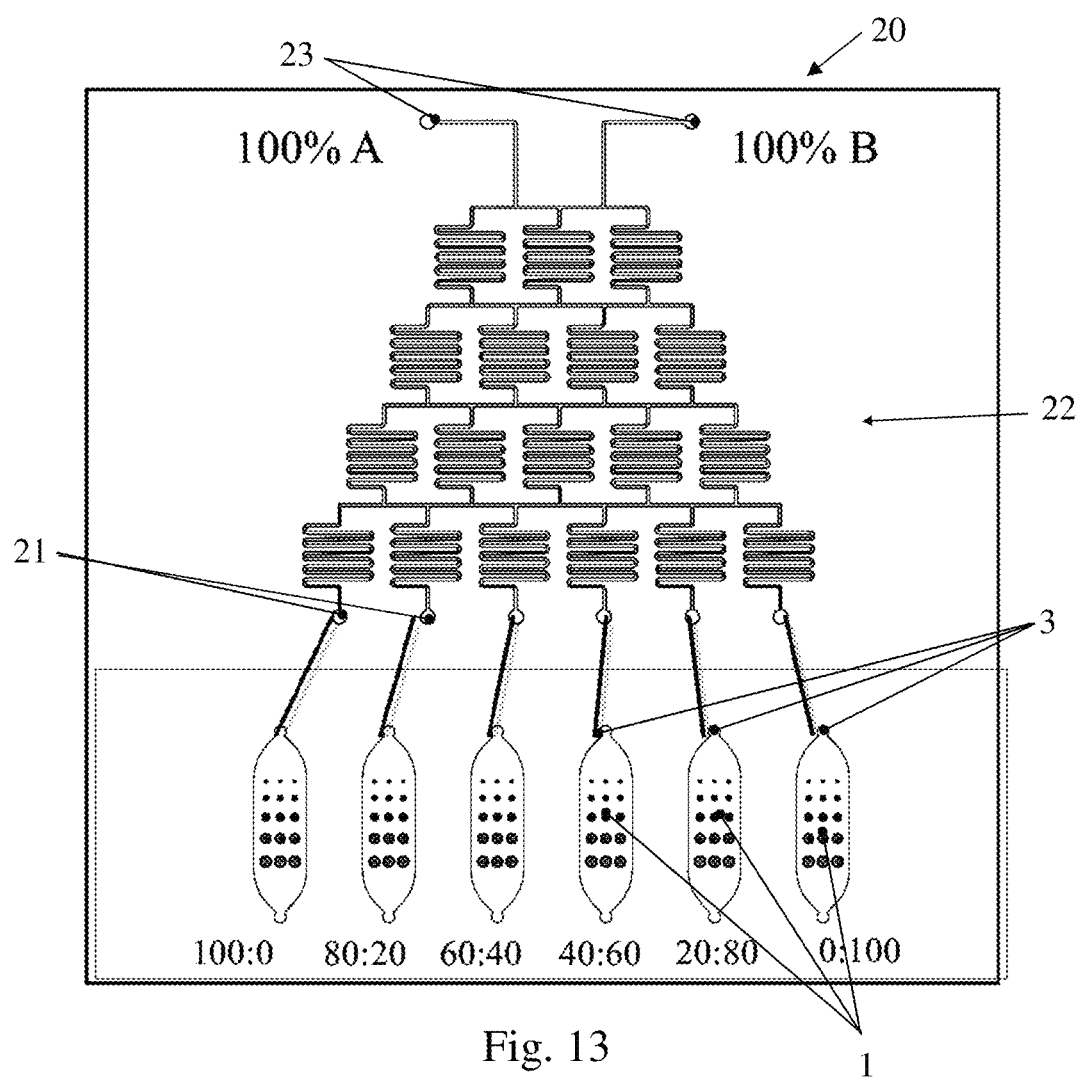
FIG. 13 shows in a schematic plan view an embodiment of a system according to the invention having six microfluidic devices according to FIG. 1 and a gradient generator.

FIG. 13 shows in a schematic plan view an embodiment of a system 20 according to the invention having six microfluidic devices 1 according to FIG. 1 and a gradient generator 22. The gradient generator 22 comprises six fluid outlets 21, wherein each fluid outlet 21 is connected to a fluid inlet 3 of a microfluidic device 1. Furthermore, the gradient generator 22 comprises two fluid inlets 23, via which fluid inlets 23 a substance A and a substance B may be supplied to the gradient generator.

By providing a substance A and a substance B at the same pressure at the fluid inlets 23 the microfluidic devices 1 are rinsed with different compounds of the substances A and B. As can be seen in FIG. 13, the compounds vary between a compound of 100% A and 0% B and a compound of 0% A and 100% B. With the system 20 it is possible to determine the influence of varying substance concentrations on cellular spheroids.

Please note, that the gradient generator 22 can also have more fluid inlets 23 and/or more or less fluid outlets 21.

Figure 14:
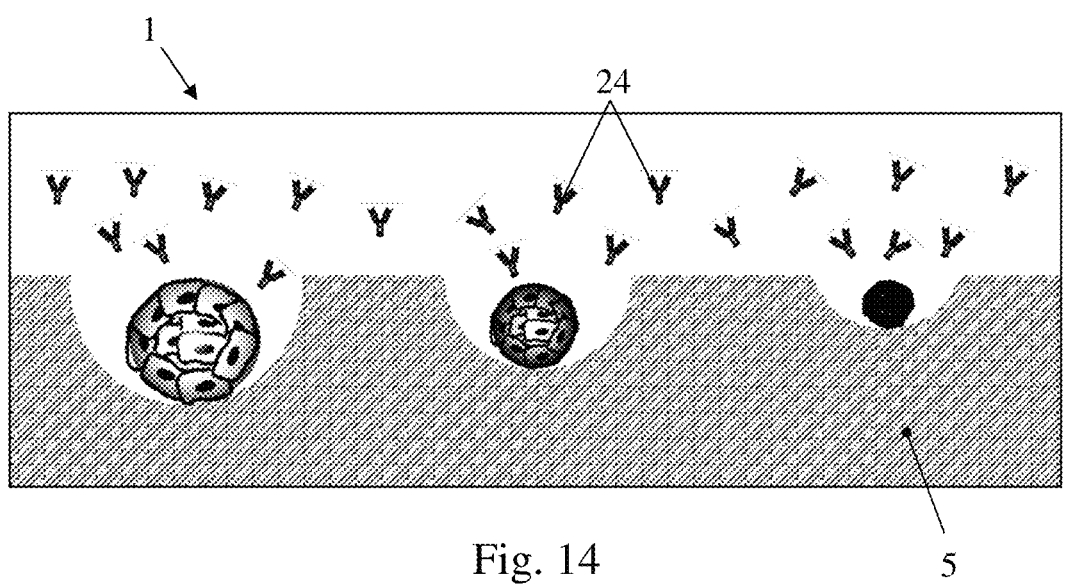
FIG. 14 shows cellular spheroids in a microfluidic device according to FIG. 9a during incubation with antibodies in a schematic view.

FIG. 14 shows cellular spheroids in a microfluidic device 1 according to FIG. 9a during incubation with antibodies 24 in a schematic view, wherein FIG. 14 only shows a part of the microfluidic device 1.

EXAMPLE

Material and Methods

Fabrication of the Microfluidic Devices 1:

The microfluidic device 1 as depicted in FIGS. 5a to 9a were fabricated by double casting of poly(dimethyl siloxane) (PDMS). The first matrix including concave microwells and channels, are made in poly(methyl methacrylate) (PMMA) using CNC micromilling PDMS is prepared by mixing the prepolymer and curing agent in a weight ratio of 10:1. The mixture is poured onto the PMMA structure placed and cured for 3 h at 75° C. The structure is peeled off from the PMMA matrix subsequently and placed in the oven for 48 h at 100° C. (thermal aging step). As a result, the second matrix with convex patterns was obtained. The thermally aged PDMS master was used for the next replica molding procedure and thus, the PDMS bottom layer of the microsystem was obtained. Holes for tubing (fluid inlet and fluid outlet) were drilled in glass slides and irreversibly bonded to the bottom PDMS layer using an oxygen plasma activation for 1 minute at 90 W. Bonding between the PDMS and glass layer was facilitated by backing the micro fluidic devices 1 for 1 h at 70° C. after alignment.

Cell Culture:

Hepatocellular carcinoma cells (ATCC, USA) were cultivated in minimal essential medium (MEM) supplemented with 10% fetal bovine serum (FBS, Gibco, USA), 1% GlutaMax™ (Life technologies, Thermo Fisher Scientific, USA) and 1% antibiotic/antimycotic solution (Sigma-Aldrich, Austria). The cells were cultivated in 75 cm² cell culture flasks under standard cell culture conditions at 37° C. in 5% $CO_2$ humidified atmosphere as adherent monolayers. At a confluency of 80%, cells were rinsed with Phosphate buffer (PBS, Sigma-Aldrich, Austria) and trypsinized for 10 min at 37° C. for enzymatic detachment. Complemented MEM was added to inactivate trypsin (GE Healthcare, Austria) and cell suspension was centrifuged at 1250 rpm for 5 min and the precipitated pellet was resuspended in fresh medium. Cell were counted and viability was carried out against Trypan Blue reagent by using an automated cell counter (Nano En Tek, Korea) before seeding.

Cell Seeding and Cellular Spheroid Generation:

After fabrication the chambers 2 of the microfluidic devices 1 as depicted in FIGS. 5a to 9a were perfused at a flow rate of 4 µL min$^{-1}$ with 70% ethanol using a syringe pump (KD Scientific, USA) for 1 hour. After flushing with sterile dH$_2$O, the chambers 2 were then loaded by an anti-fouling protein solution with a flow rate of 1 µL min$^{-1}$ and incubated over night at room temperature to create a nanobiointerface that prevents cell adhesion and induces controlled cellular spheroid generation in each recess 6. The protein solution is removed by flow injection of cell culture media followed by a cell seeding step. Single cell suspension at a density of 6×10$^6$ cells mL$^{-1}$ was loaded into the chambers 2 using a syringe pump at flow rate of 4 µL min$^{-1}$ for 10 min After one hour of incubation, non-trapped cells were eluted by cell culture medium at a flow rate of 10 µL min$^{-1}$. Cellular spheroid cultivation in the recesses 6 is conducted at constant flow rate of 4 µL min$^{-1}$ at 37° C. and 5% CO$_2$.

Image Analysis:

Micrographs of the microfluidic devices 1 as depicted in FIGS. 5a to 9b were analyzed with an image processing and analysis freeware (ImageJ, NIH, USA). Spheroid cultivation was monitored over 3 days with an inverted fluorescence optical microscope (TE2000, Nikon, Japan) equipped with a digital camera (DS-Qi1MC, Nikon, Japan). Spheroid area, perimeter, solidity and roundness were measured by using the BioVoxxel Image Processing and Analysis Toolbox for ImageJ (Biovoxxel, Germany) Data were expressed as mean±standard deviation (SD). All experiments were done independently in triplicates.

Results

To evaluate the optimal shape of a recess 6 for precise size control of reproducible, uniform-sized, single HepG2 cellular spheroids, variable recess shapes and sizes were tested. In particular, recesses 6 of the shape of a cylinder (100 µm and 500 µm depth), a spherical cap, an elliptic paraboloid and a hemisphere were tested. After 3 days post-seeding morphology of HepG2 cellular spheroids was evaluated. FIG. 10 shows the impact of the recess shapes on the number of generated HepG2 cellular spheroids in dependence of a recess diameter. The results indicate that hemispherical recesses resulted in the formation of single spheroids within each of the recess independent of recess diameter. In contrast, recesses with different curvatures as well as cylindrical shapes showed a higher probability to form multiple spheroids in each cavity, thus decreasing spheroid production yield and accuracy.

To assess the influence of recess shape on the quality of spheroid morphology, roundness factor of each micro-tissue was determined for recesses having the shape of a cylinder (100 µm and 500 µm depth), a spherical cap and a hemisphere. FIG. 11 shows that hemispherical- and the spherical cap-shape induced the formation of reproducible round HegG2 spheroids in each well diameter. Additionally, the elliptical paraboloid shape with a shell surfaces of the paraboloids formed by parables with the formula $y=A*x^B$ with A between 0.14 and 0.3 and B between 2 and 4 resulted in formation of round single HepG2 spheroids comparable to the hemispherical and spherical cap shaped recesses, however, with elliptical paraboloid shaped recesses with a shell surfaces different of that a reduction in roundness was observable. Spheroids with a roundness factor above 0.9 are considered as regular spherical shaped micro-tissues as described in literature (see Zanoni et al (Sci Rep. 2016; (6): 19103).

In contrast, both of the cylindrical shape resulted in irregular non-circular HepG2 spheroids. To investigate these effects in more detail, spheroid size controllability for recesses with a hemispherical, elliptic paraboloid a spherical cap shape was evaluated. Hemispherical recesses showed the ability to adjust spheroid size in a reproducible manner as shown in FIG. 12. The hemispherical shape led to a linear increase of spheroid size within a single microchannel channel, whereas elliptical paraboloid- and spherical cap shaped recesses resulted in an irregular and less controllable formation of spheroids (no linear increase and correlation).

CONCLUSION

Here, we show a novel method and device for size control of cellular spheroid generation within a single microchannel based on the influence of recess shape and diameter in a microfluidic device. We showed that cylinder-shaped recesses enable the formation of multiple non-regular cellular spheroids and therefore, these shapes can be considered as unpredictive architecture for precise micro-tissue size control. Further recess shapes as elliptic paraboloid, spherical cap and hemispherical recess were evaluated regarding optimal cell trapping efficiency as well as resulting formation of size-tunable round cellular spheroids. In conclusion, hemispherical recesses lead to the generation of reproducible single cellular spheroid in each individual recess with 100% yield with high controllability in spheroid size and morphology.

The microfluidic device of the present invention is a rapid evaluation tool for determining the optimal spheroid size for toxicology screenings, stem cell research, tissue engineering and biochemical staining protocols which are the basis for reliable and robust data. In summary, the microfluidic device according to the invention is a facile tool for screening spheroids of different sizes produced by geometric control of micro-recesses, which demonstrates the optimal spheroid size for a broad range of applications.

The invention claimed is:

1. A method for the production of cellular spheroids comprising the steps of:
    applying a fluid comprising biological cells into at least one chamber (2; 9) of a microfluidic device (1; 8), wherein the microfluidic device (1; 8) comprises at least one chamber (2; 9) comprising a fluid inlet (3) for introducing fluid into the chamber (2; 9) and a fluid outlet (4) for removing said fluid from the chamber (2, 9), wherein said at least one chamber (2; 9) comprises a base formed by a substrate (5;10) comprising at least two recesses (6; 11) to collect a fluid comprising biological cells when the substrate (5, 10) is contacted with the fluid, wherein the size of the at least two recesses (6; 11) decreases from the fluid inlet (3) to the fluid outlet (4) of the at least one chamber (2; 9), and thus providing said fluid to at least two recesses (6; 11) of the device; and
    incubating the device (1; 8) comprising said fluid for at least 2 hours until at least one cellular spheroid is formed in the at least two recesses (6; 11),
    wherein the cellular spheroids are eluted by successively rinsing the at least one chamber (2; 9) with a discharging fluid with different velocities.

2. The method according to claim 1, wherein the device (1; 8) comprising said fluid is incubated for a maximum of six months.

3. The method according to claim 1, wherein the device (1; 8) comprising said fluid is incubated for one to seven days.

4. The method according to claim 1, wherein the fluid comprising biological cells is applied into the at least on chamber (2; 9) with a velocity in a range of 4 µL/min to 8 µL/min.

5. The method according to claim 1, wherein the at least one cellular spheroid formed in at least two recesses (6; 11) is eluted by rinsing the at least one chamber (2; 9) with a discharging fluid at a velocity sufficient to elute the cellular spheroid.

6. The method according to claim 5, wherein the velocity for eluting the spheroid(s) is in a range of 0.5 µL/min to 120 µL/min.

7. The method according to claim 1, wherein the cellular spheroids within the at least two recesses (6, 11) are incubated with at least one antibody (24) binding specifically to the biological cells forming the cellular spheroids.

8. The method according to claim 1, wherein the fluid inlet (3) and the fluid outlet (4) are positioned to direct fluid flowing from the fluid inlet (3) to the fluid outlet (4) through the chamber (2; 9).

9. The method according to claim 1, wherein the substrate (5; 10) comprises, consists of or is coated with a biocompatible material.

10. The method according to claim 9, wherein the biocompatible material is a silicone or a plastic material or glass.

11. The method according to claim 1, wherein the at least two recesses (6; 11) have the shape of a hemisphere, a spherical cap, a semi ellipsoid, a cone, a truncated cone, a terraced cone, a pyramid, a truncated pyramid, a terraced pyramid, a torus, or an elliptic paraboloid.

12. The method according to claim 1, wherein the at least two recesses (6; 11) have a depth of 50 µm to 1 mm.

13. The method according to claim 1, wherein the at least two recesses (6; 11) have a width or diameter of 100 µm to 2 mm.

14. The method according to claim 1, wherein the ratio of depth to width of the at least two recesses (6; 11) is between 1 to 1 and 1 to 3.

15. The method according to claim 1, wherein the at least two recesses (6; 11) have a different size and shape.

16. The method according to claim 1, wherein the at least two recesses (6; 11) are spaced apart from each other at a distance from 10 µm to 6 mm.

17. The method according to claim 1, wherein the at least two recesses (6; 11) are grouped and the recesses (6; 11) of each group (7a-7e) have the same size and/or the same shape and the recesses (6; 11) of different groups (7a-7e) have different sizes or different sizes and different shapes.

18. The method according to claim 1, wherein the at least one chamber (9) rejuvenates from the fluid inlet (3) to the fluid outlet (4).

* * * * *